(12) United States Patent
Jones et al.

(10) Patent No.: US 8,695,443 B1
(45) Date of Patent: Apr. 15, 2014

(54) SCREENING SYSTEM AND METHOD OF USING SAME

(75) Inventors: David A. Jones, Sandia Park, NM (US); Christopher A. Gresham, Albuquerque, NM (US); Marc L. Basiliere, Albuquerque, NM (US); James J. Spates, Albuquerque, NM (US); Philip J. Rodacy, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 398 days.

(21) Appl. No.: 12/871,327

(22) Filed: Aug. 30, 2010

(51) Int. Cl.
*G01N 1/22* (2006.01)

(52) U.S. Cl.
USPC ..................................... 73/863.12

(58) Field of Classification Search
None
See application file for complete search history.

(56) References Cited

U.S. PATENT DOCUMENTS

| | | | |
|---|---|---|---|
| 4,698,071 A | 10/1987 | Elias | |
| 5,092,156 A | 3/1992 | Miskolczy | |
| 5,289,715 A * | 3/1994 | Staples et al. | 73/24.01 |
| 5,321,888 A * | 6/1994 | Nemes | 29/890.054 |
| 5,386,788 A | 2/1995 | Linker et al. | |
| 5,500,369 A * | 3/1996 | Kiplinger | 435/309.1 |
| 5,753,832 A | 5/1998 | Bromberg | |
| 5,760,314 A | 6/1998 | Bromberg | |
| 5,854,431 A | 12/1998 | Linker et al. | |
| 5,859,362 A | 1/1999 | Neudorfl | |
| 5,915,268 A | 6/1999 | Linker et al. | |
| 6,083,360 A | 7/2000 | Ohlhausen et al. | |
| 6,085,601 A | 7/2000 | Linker et al. | |
| 6,171,378 B1 | 1/2001 | Manginell et al. | |
| 6,326,615 B1 | 12/2001 | Syage et al. | |
| 6,334,365 B1 | 1/2002 | Linker et al. | |
| 6,345,545 B1 | 2/2002 | Linker et al. | |
| 6,354,160 B1 * | 3/2002 | Staples et al. | 73/863.12 |
| 6,477,907 B1 | 11/2002 | Chambers et al. | |
| 6,523,393 B1 | 2/2003 | Linker et al. | |
| 6,572,825 B1 | 6/2003 | Linker et al. | |
| 6,604,406 B1 | 8/2003 | Linker et al. | |

(Continued)

OTHER PUBLICATIONS

Karl A. Hanold, "Mass Spectrometry Base Personnel Screening Portal," Proceedings of the 7th International Symposium in the Analysis and Detection of Explosives, Edinburgh, Scotland, pp. 13, Jun. 25-28, 2001.

(Continued)

*Primary Examiner* — Robert R Raevis
(74) *Attorney, Agent, or Firm* — Michael A. Beckett

(57) ABSTRACT

An integrated apparatus and method for screening an object for a target material is provided. The integrated apparatus comprises a housing and an integrated screener. The housing is positionable adjacent the object, and has a channel therethrough. The integrated screener is positionable in the housing, and comprises a fan, at least one filter, a heater and an analyzer. The fan is for drawing air carrying particles and vapor through the channel of the housing. The filter(s) is/are positionable in the channel of the housing for passage of the air therethrough. The filter(s) comprise(s) at least one metal foam having a plurality of pores therein for collecting and adsorbing a sample from the particles and vapor passing therethrough. The heater is for applying heat to the at least one metal foam whereby the collected sample is desorbed from the metal foam. The analyzer detects the target material from the desorbed sample.

18 Claims, 6 Drawing Sheets

(56) References Cited

U.S. PATENT DOCUMENTS

| | | | |
|---|---|---|---|
| 6,617,591 | B1 | 9/2003 | Simonson et al. |
| 6,806,450 | B2 * | 10/2004 | Nakashige et al. ............ 250/288 |
| 6,848,325 | B2 | 2/2005 | Parmeter et al. |
| RE38,797 | E | 9/2005 | Linker et al. |
| 6,978,657 | B1 | 12/2005 | Baumann et al. |
| 7,119,342 | B2 | 10/2006 | Syage et al. |
| 7,141,786 | B2 * | 11/2006 | McGann et al. ............... 250/287 |
| 7,144,445 | B2 * | 12/2006 | Gueret et al. ..................... 95/96 |
| 7,299,711 | B1 | 11/2007 | Linker et al. |
| 7,338,638 | B2 * | 3/2008 | McGann et al. ................. 422/78 |
| 7,401,498 | B2 | 7/2008 | Syage et al. |
| 7,407,633 | B2 * | 8/2008 | Potember et al. .............. 422/121 |
| 7,430,928 | B2 * | 10/2008 | Grate et al. ................. 73/863.21 |
| 7,449,050 | B2 * | 11/2008 | Wohltjen et al. ................ 95/148 |
| 7,605,709 | B2 * | 10/2009 | Tolliver ...................... 340/573.1 |
| 2004/0022670 | A1 | 2/2004 | Megerle et al. |
| 2006/0271211 | A1 | 11/2006 | Gleason |
| 2007/0138387 | A1 | 6/2007 | Syage et al. |

OTHER PUBLICATIONS

Kevin L. Linker, "Explosives Detection Personnel Portals," Counterterrorist Detection Techniques of Explosives, Chapter 12, pp. 367-393 (2007).

Jehuda Yinon, "Personal Screening Booths (Portals)", Forensic and Environmental Detection of Explosives, John Wiley and Sons, West Sussex, Section 2.10, p. 75-79 (1999).

K.L. Linker, "Large-Volume Sampling and Preconcentration", 3rd Explosives Detection Technology Symposium and Aviation Security Technology Conference, Atlantic City, NJ, p. 1-10, 2001.

J.E. Parmeter et al, "Testing of a Walk-Through Portal for the Trace Detection of Contraband Explosives", Proceedings of the 2nd Explosives Detection Symposium & Aviation Security Conference, Atlantic City, NJ, p. 187-192, (1996).

Jay W. Grate, Norman C. Anheier and David L. Baldwin, "Progressive Thermal Desorption of Vapor Mixtures From A Preconcentrator With A Porous Metal Foam Internal Architecture and Variable Thermal Ramp Rates" in "Analytical Chemistry," vol. 77, Issue: 6 (Mar. 15, 2005), pp. 1867-1875.

* cited by examiner

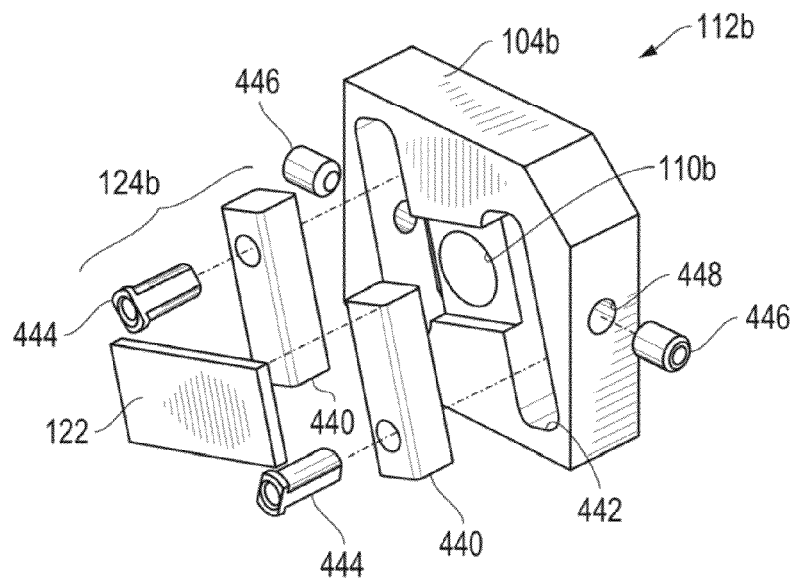
FIG. 4A
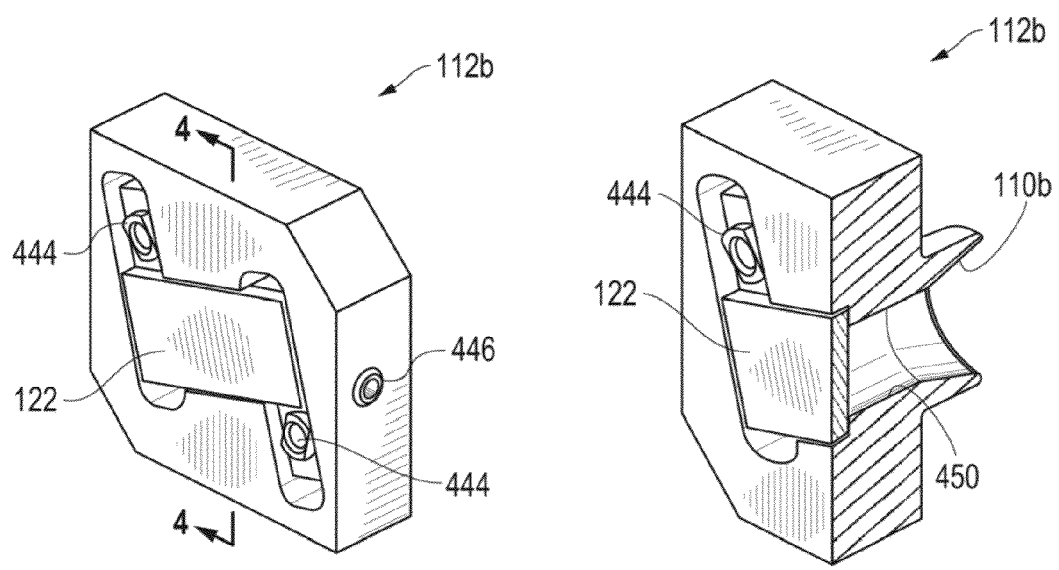
FIG. 4B
FIG. 4C

SCREENING SYSTEM AND METHOD OF USING SAME

STATEMENT OF GOVERNMENT INTEREST

This invention was developed under Contract DE-AC04-94AL85000 between Sandia Corporation and the U.S. Department of Energy. The U.S. Government has certain rights in the invention.

BACKGROUND OF THE INVENTION

The present invention relates to techniques for screening objects. More particularly, the present invention relates to techniques for screening (e.g., collecting, sampling, detecting, analyzing, etc.) objects for the presence of certain materials, such as controlled substances.

Controlled substances, such as explosives (e.g. C4, TNT, dynamite, fuels, chemicals, casted and/or other volatile materials), contraband (e.g. illegal drugs), chemical agents (e.g. toxins), etc., may pose a significant threat to persons and/or property. In an effort to prevent the unauthorized use or possession of such controlled substances, steps are often taken to locate target materials (e.g., materials used in connection with and/or incorporated in such controlled substances) before they can be used. Materials not used in connection with controlled substances may also be target materials. In many cases, such target materials may be hidden or stored to prevent detection, or are only present in small volumes.

Techniques have been developed in an attempt to detect the presence of certain target materials. Some techniques involve off-line laboratory analysis, such as monitoring environmental pollutants and in industrial hygiene monitoring. Other techniques involve on-line processes, such as detection systems used at checkpoints to interrogate personnel or vehicles for the target materials. Interrogation often involves the collection of materials from persons or objects using various collectors, such as volume, thin foil and membrane filters. Foam or other porous materials may be employed as described, for example, in U.S. Pat. No. 7,430,928, and in Grate, Anheier and Baldwin, *Progressive Thermal Desorption Of Vapor Mixtures From A Preconcentrator With A Porous Metal Foam Internal Architecture And Variable Thermal Ramp Rates in Analytical Chemistry*, Volume: 77, Issue: 6 (Mar. 15, 2005), pp. 1867-75.

Once the material is collected, it may then be released into small volumes for introduction into a detection system in a process known as pre-concentration. Techniques, such as preconcentrators, have been developed for handling trace amounts of materials as described, for example, in US Patent/Application Nos. 20060271211, U.S. Pat. Nos. 6,948,325, 6,617,591, 6,477,907, 7,299,711, 6,345,545, 6,617,591, 6,604,406, 6,572,825, 6,523,393, 6,085,601, RE38,797, 5,854,431, 6,978,657, and 6,171,378. The pre-concentrated material may then be examined by a detector to determine if the target material is present. Detectors have been developed to identify the presence of explosive materials as described, for example, in US Patent/Application No. 20060271211, U.S. Pat. Nos. 6,978,657, 6,948,325, 6,617,591, and 6,477,907. Some techniques involve the use of handheld devices as described, for example, in U.S. Pat. Nos. 5,092,156 and 6,978,657.

Despite the development of techniques for collecting, pre-concentrating or detecting certain materials, there remains a need to provide advanced systems and methods for screening for such materials. It may be desirable to have techniques that perform integrated operations. It may further be desirable to provide techniques that enable screening of materials in a variety of locations and/or positions. Preferably, such techniques involve one or more of the following, among others: low cost design and ease of use.

BRIEF DESCRIPTION OF THE DRAWINGS

So that the features and advantages of the present invention can be understood in detail, a more particular description of the invention may be had by reference to some embodiments thereof that are illustrated in the appended drawings. These drawings are used to illustrate only some typical embodiments of this invention, and are not to be considered limiting of its scope, for the invention may admit to other equally effective embodiments. The figures are not necessarily to scale and certain features and certain views of the figures may be shown exaggerated in scale or in schematic in the interest of clarity and conciseness.

In FIG. 1A, the system comprises a screening portal. In FIG. 1B, the system comprises a screening wand.

FIG. 3A is an exploded view of the integrated screener from a first direction. FIG. 3B is the exploded view the integrated screener from a second direction.

FIGS. 4A-4C are exemplary schematic depictions of the integrated screener of FIG. 1B, having an electrode heater. FIG. 4A is an exploded view of the integrated screener.

FIG. 5A is a plan view of a magnified portion of the metal foam. FIG. 5B is an end view of the magnified metal foam of FIG. 5A.

DETAILED DESCRIPTION OF THE INVENTION

Presently preferred embodiments of the invention are shown in the above-identified Figures and described in detail below.

Figure 1A:
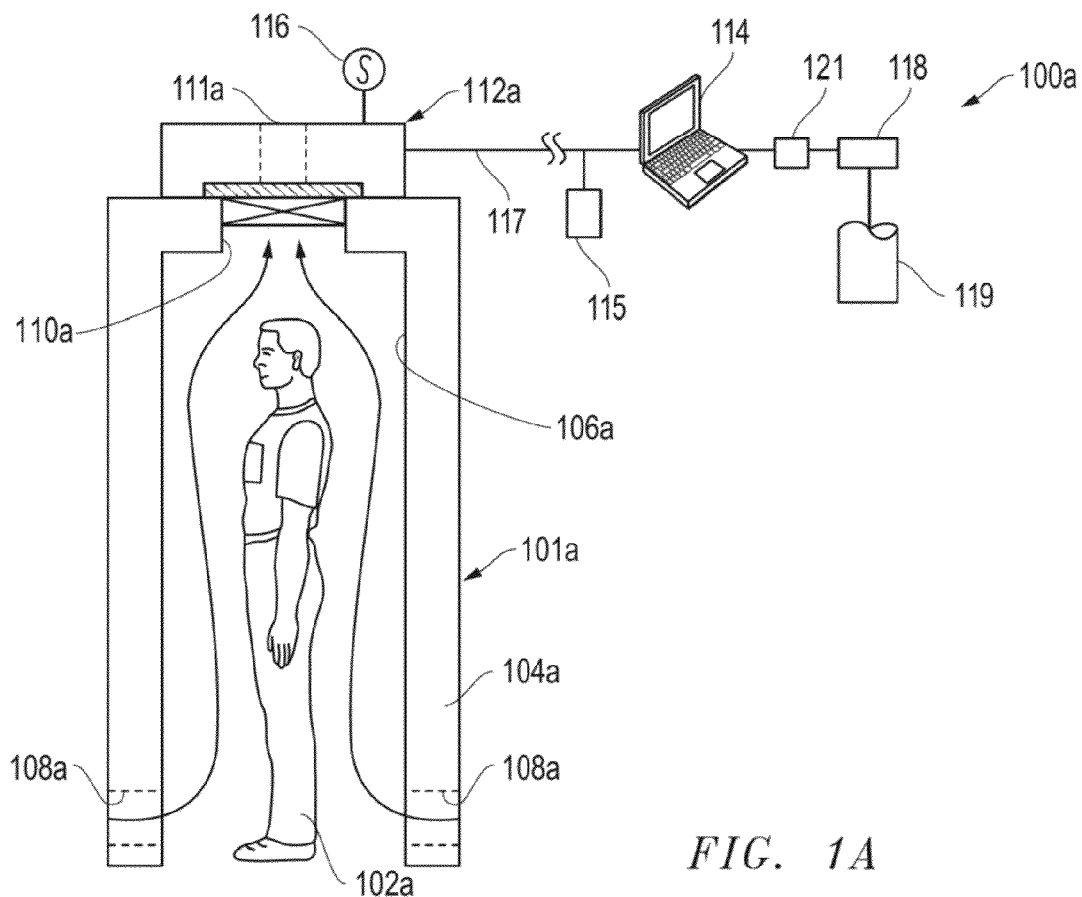
FIGS. 1A-1B are exemplary schematic depictions of a system for screening an object, each system comprising an integrated screener.
Figure 1B:
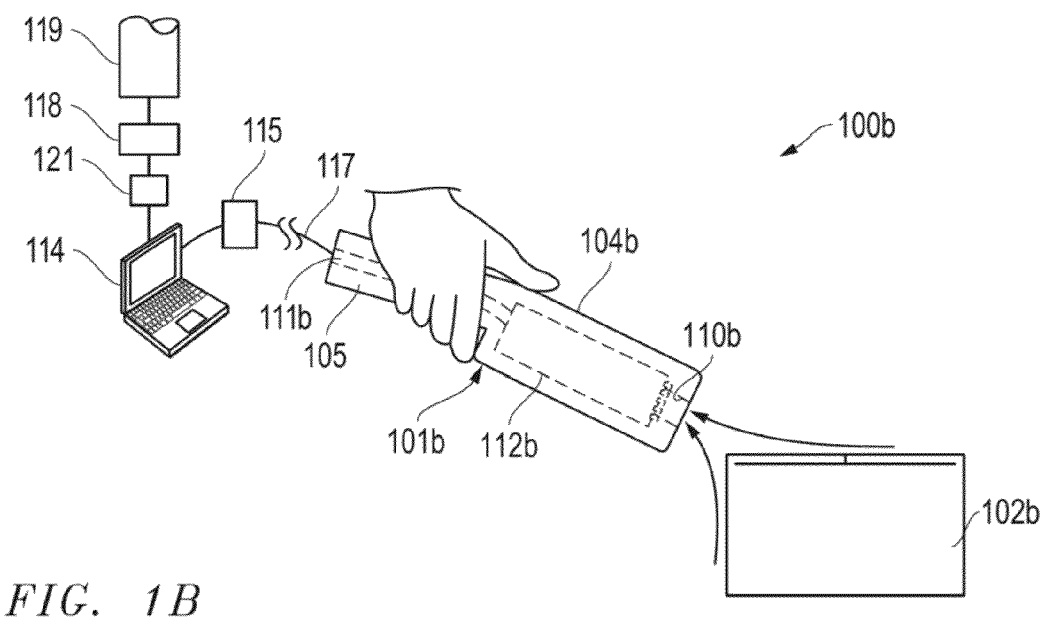

FIGS. 1A and 1B are schematic diagrams depicting exemplary systems 100a,b for screening an object 102a,b, respectively. The system 100a,b preferably has integrated screening capabilities that permit the performance of multiple functions in a single operation within the same system. Such integrated screening may involve, for example, the collection, sampling, detection and/or analysis, of material about the object. Preferably, the system 100a,b is capable of sampling materials in any form, such as any vapor and/or particles.

The integrated sampling system 100a as shown in FIG. 1A includes is a screening apparatus or portal 101a that may be used for removing material from an object, such as a person 102a. The portal 101a has a housing 104a with a chamber 106a for receiving the person 102a and collecting samples therefrom. Fluids, such as air or other gases (referred to herein as 'air') may be passed into portal 101a via ports 108a, over the person 102a and through inlet 110a as indicated by the arrows. As air is passed over the person 102a, materials in the form of vapor and/or particles are removed from the object and passed along with the air through inlet 110a.

The integrated system 100a further includes an integrated screener 112a for screening material from the object 102a. The integrated screener 112a is depicted as being positioned on top of the portal 100a and in fluid communication with portal 100a via an inlet 110a therein. However, it will be appreciated that the integrated screener 112a may be located anywhere for receipt of the air passed over the person 102a as indicated by the arrows. The integrated screener 112a is preferably capable of receiving the material (e.g., vapor and/or particles) carried by the air as it passes through inlet 110a. After passing through integrated screener 112a, the air (less any retained material, such as particles and/or vapor) may exit through outlet IIia.

The integrated sampling system 100b as shown in FIG. IB includes a screening apparatus or screening wand 101b that may be used for screening material from an object, such as an object (or box) 102b. The screening wand 101b has a housing 104b positionable adjacent the object 102b for collecting samples therefrom Air adjacent the object 102b may be drawn into screening wand 101b through inlet 110b as indicated by the arrows. As air is passed over the object 102b, material (e.g., vapor and/or particles) are removed from the object 102b, passed through inlet 110b and into the screening wand 100b.

The integrated system 100b further includes an integrated screener 112b for screening for certain materials about the object 102b. The integrated screener 112b is preferably capable of receiving the material (e.g., vapor and/or particles) carried by the air as it passes through screening wand 101b.

The screening wand 101b comprises a housing 104b with a handle 105 for handheld operation. As shown, the screening wand 101b is gripped by a person and positionable adjacent to the object 102b. The integrated screener 112b is depicted as being positioned within the screening wand 101b and in fluid communication with the inlet 110b therein. However, it will be appreciated that the integrated screener 112b may be positioned anywhere about the object 102b for receipt of the air passed over the object 102b and material drawn therefrom as indicated by the arrows.

The screening portal 101a and/or screening wand 101b may be operatively connectable to other devices, such as processor 114, a power supply 115, communicator 118, database 119, alarm 121 and/or other electrical devices. Links 117, such as cable, wireless or other conventional connectors, may be provided to electrically connect the systems 100a and/or 100b to such electrical devices for the passage of power and/or communication signals therebetween. Alarm 121 may be used to sound upon detection of the target material or other event. Some or all such electronic devices may be incorporated within the systems 100a,b and/or integrated screeners 112a,b.

Processor 114 may be used to further evaluate data collected from by the systems 100a and/or 100b. The material collected and/or data generated from the screener may be used to generate reports and/or process external data with data collected by the systems 100a,b. The external data may, for example, provide information about the object, the target material, historical data and/or other information that may be used in combination with data collected by systems 100a,b.

The power supply 115 may be an external power source, such as an electrical motor, or an internal power source, such as a battery. The screening portal and/or wand 101a,b may be provided with links 117 that operatively connect to the external power source. Preferably, the screening portal and/or wand 101a,b may be powered for remote and/or portable use. Detachable connectors (not shown) may be provided to selectively connect to external electronics, such as the power supply.

Figure 2:
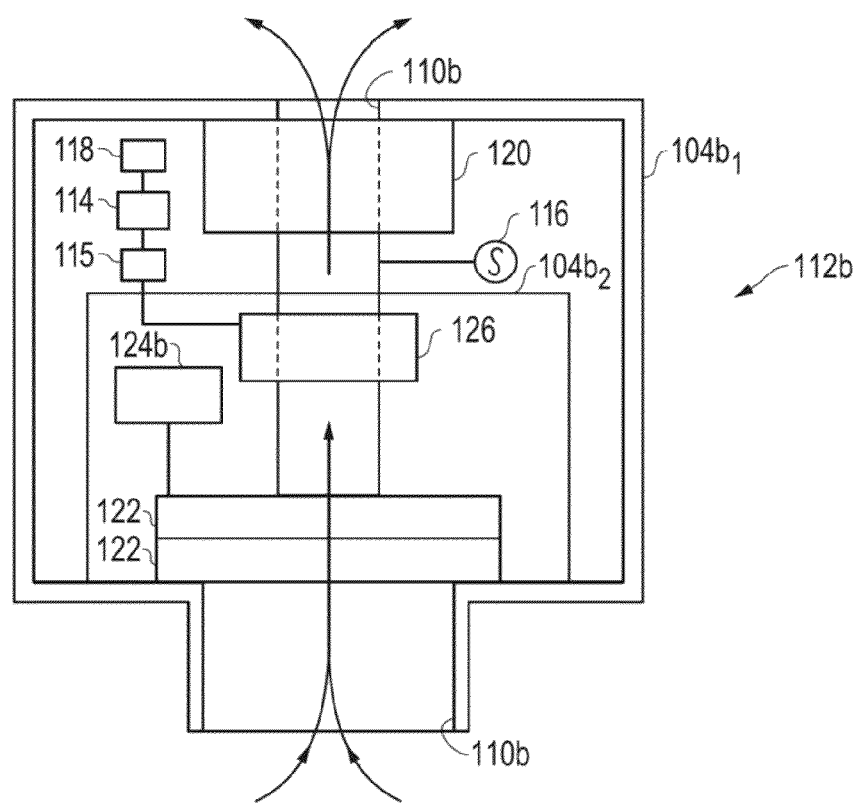
FIG. 2 is a schematic view of the integrated screener of FIG. 1B.

FIG. 2 is a schematic view depicting components of an integrated screener usable as, for example, the integrated screener 112b of FIG. 1B. The integrated screener 112b may be, for example, a solid foam material collector used as a pre-concentrator. The integrated screener 112b comprises a fan (or air pump) 120, a pair of filters 122, heater 124b and an analyzer 126. As depicted in FIG. 2, other components, such as processor 114, power supply 115, sensor 116 and communicator 118, may also be housed in housing 104b for integrated operation therein.

Air entering inlet 110b and passing into the integrated screener 112b is passed through the filters 122. The filters 122 are preferably configured to capture vapor and/or particles from the air passing therethrough.

Particles and vapors may be removed from the filter 122 by washing the filter with a liquid, dissolving the particles and vapors with a solvent, and/or thermally desorbing the particles and vapor into a carrier gas. For thermal desorption, the filter 122 may be heated by the heater 124. Once heated, the particles are desorbed and condensed into a sample received by analyzer 126. As depicted, the heated filter 122 is preferably capable of desorbing the vapor and particles. However, if desired, liquid, such as a sorbent or other solvent, may be positioned in the filter to capture the vapor and particles.

Analyzer 126 collects data from the samples to detect pre-defined materials in the sample. The analyzer may be any detector capable of detecting a pre-determined material in the particle and/or vapors in the air passing through the integrated screener 112b. Examples of detection techniques that may be used involve ion mobility spectrometry, electron capture device, gas chromatograph, chemiluminescence, mass spectroscopy, ion trap mobility spectroscopy, thermo redox, and the like. Examples of pre-concentrators that may be employed are described in U.S. Pat. Nos. 6,085,601 and RE38,797, the entire contents of which are hereby incorporated by reference. The air passing through the filters 112b and analyzer 126 may continue through the integrated screener 112b past fan 120 and out outlet 110b.

One or more filters may be used to achieve the desired samples. For example, multiple foams and/or other filters may be stacked to provide the desired capture of particles. Where multiple foams are used, the pore size may be the same or different for the various foams used. The size, shape, material, configuration and/or pore size of the metal foam may be selected to provide the desired functionality. An example of a selected configuration may be a metal foam with a 300 micron nominal pore size and a nominal thickness of about 1 mm.

As shown, the integrated screener 112b may be integrated into a housing 104b1 and/or 104b2 for performing a combination of screening functions, such as the collection, sampling, detection and/or analysis, of material on the object. Preferably, components positioned in housing 104b1 and/or b2 are capable of performing integrated screening functions, such as more than one of sampling, collecting, detecting, analyzing. Preferably, the housing 104b1 and/or b2 provides a portable unit usable as or positionable in a desired screening system. The integrated functionality is intended to provide a portable system capable of performing multiple screening functions in a unitary entity. This integrated functionality may also be used to permit multiple functions to be performed in close proximity to each other, and under similar environmental conditions for consistency.

Figure 3A:
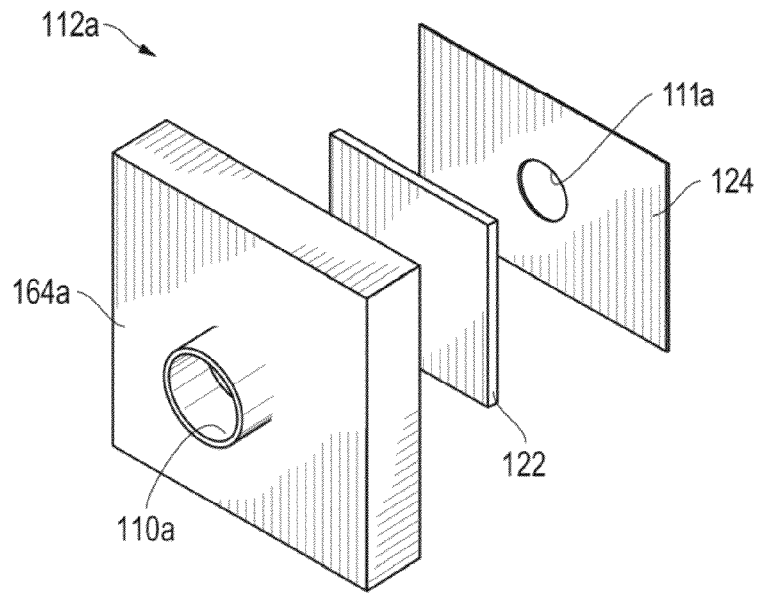
FIGS. 3A and 3B are schematic depictions of the integrated screener of FIG. 1A, having a resistance heater.
Figure 3B:
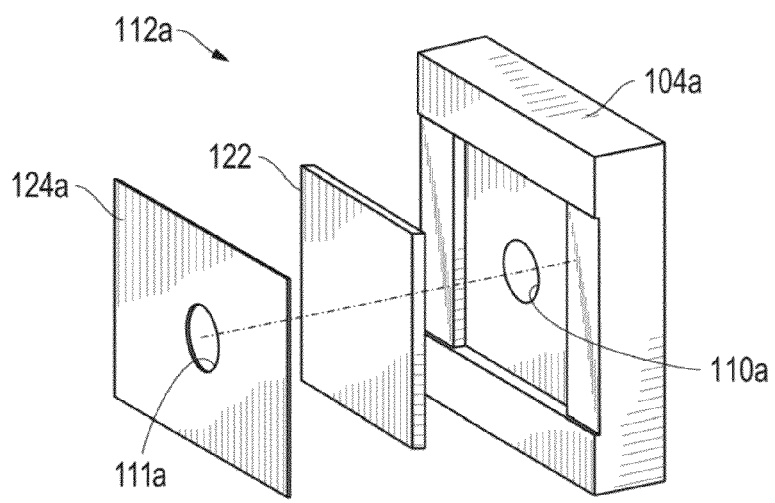

FIGS. 3A and 3B are exploded views of the integrated screener 112a of FIG. 1A taken from a first and a second direction. In this configuration, the integrated screener 112a has a housing 104a, a filter 122 and a heater 124a. The housing is depicted as a rectangular box for receiving the filter 122 and the heater 124a. Connectors, adhesives or other devices (not shown) may be provided to secure components within the housing 104a.

The filter 122 is positionable adjacent the housing 104a and across inlet 110a such that air passing into inlet 110a passes through filter 122. The heater 124a as depicted may be a resistance heater capable of heating the filter 122 sufficient to desorb the vapor and particles therefrom. The resistance heater 124a is preferably capable of resistively heating the filter 122 by passing and electric current therethrough. While a conventional electrical resistance heater 124a is depicted, any type of heating source may be used. The resistance heater 124a is depicted as having an outlet I11a therethrough. Air passing from inlet 110a and through filter 122 exits through outlet I11a.

FIGS. 4A-4C are various views of a portion of an integrated screener usable as the integrated screener 112b of FIG. 1B. FIGS. 4A-4C depict exploded, assembled and cross-sectional assembled views, respectively, of the integrated screener 112b. In the configuration as shown in these views, the integrated screener 112b has one filter 122 and the heater 124b integrated in housing 104b. The housing 104b is preferably made of a non-conductive material, such as ceramic, that may be stable at temperatures of about 200 or more degrees Celsius.

The heater 124b may be, for example, electrodes 440 positioned in a cavity 442 in the housing 104b. The electrodes 440 are preferably copper for providing electrical resistance connections to the filter 122. The filter 122 may be resistably heated by the electrodes 440 by passing an electric current therethrough. Bolts 444 are preferably electrical connectors used to operatively (e.g., mechanically and electrically) connect electrodes 440 to a power supply, such as power supply 115 of FIG. 2. Fasteners, such as set screws 446, are preferably positionable in holes 448 in the housing 104b for retaining filter 122b therein.

The integrated screeners 112a,b of FIGS. 3A-B and 4A-C may be provided with the analyzer 126 (FIG. 2). The analyzer 126 may be incorporated into and/or connected to the housing 104a,b for receiving the desorbed vapor and particles from the filter 122 for analysis. Preferably, the housings 104a,b provide an integrated housing for containing multiple screening functions, such as those described with respect to FIG. 2.

Figure 5A:
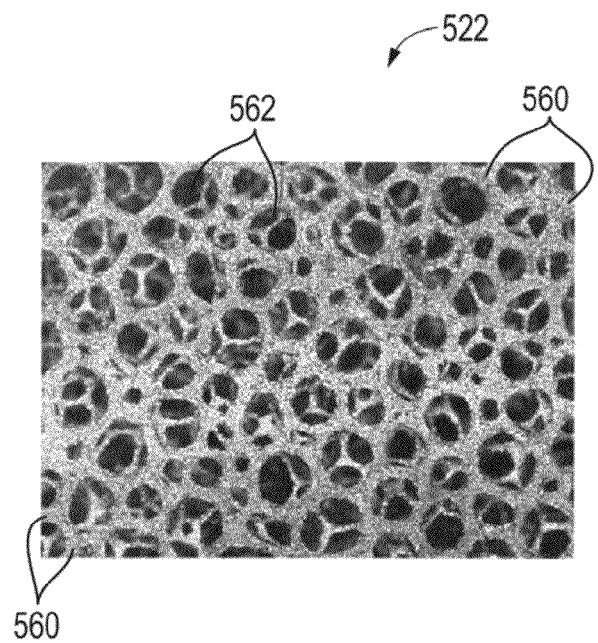
FIGS. 5A and 5B are exemplary schematic depictions of a metal foam.
Figure 5B:
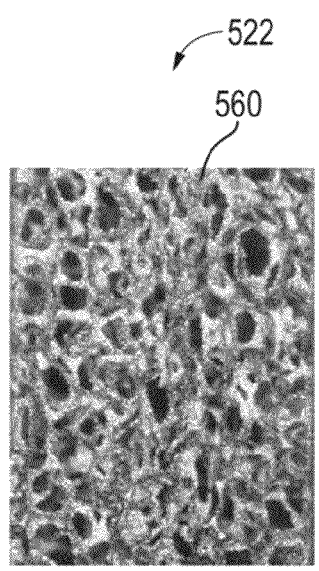

FIGS. 5A-5B depict a foam 522 that may be used as the filter 122 of FIGS. 1A-4C. FIG. 5A is a top view of a portion of the foam 522 at 100× magnification. FIG. 5B is an end view of the foam 522 of FIG. 5A. As shown in these figures, the foam 522 preferably is a solid foam with a uniform, rectangular shape with a thickness of about 1 mm and an aspect ratio of about 2 to 1. While any shape may be used, the rectangular shape with straight edges is preferred to allow current to evenly heat the foam 522 and to properly desorb particles and vapors from the metal foam 522. The foam 522 may be used in combination with other filters, such as screens, nets or felts with strands of material woven, sintered, or layered to form a semi-permeable barrier.

The metal foam 522 is provided with a plurality of edges 560. To prevent compression of the edges and/or loss of uniformity of the metal conductivity that may be caused by conventional cutting, the edges 560 are preferably cut using, for example, electrical discharge machining (EDM). EDM (or spark machining) involves the removal (or cutting) of material by discharging current between electrodes with a dielectric charged liquid therebetween. While conventional cutting may be used, in some cases, such cutting may crush, melt or fuse the cut edges of foam 522.

As shown, the foam 522 is a permeable solid foam having a plurality of inter-connected pores 562 in an open cellular structure. The foam 522 forms a three-dimensional net-like structure that is preferably capable of capturing various forms of material, such as both particles and vapor, suspended in the air passing through the integrated screener 112a,b. One or more metal foams 522 made in thin sheets with very high porosity and surface areas are preferably used. Preferably, the metal foams 522 employed have higher surface area and low pressure losses compared with other filters of the same thickness.

Metallic solid foams, such as pure metals (e.g., aluminum, copper, nickel, gold, silver), metal alloys/stainless steel (e.g., SUS316L, SUS301S), nickel alloys (e.g., heat resistant nickel-chrome-tungsten-molybdenum alloy, nickel-chrome-ferric alloy, corrosion resistant alloys-nickel-chrome-molybdenum alloy), may be employed. The metal foam used may be, for example, metal foams commercially available from MITSUBISHI MATERIALS CORPORATION™ of Tokyo, Japan (see e.g., http://www.mmc.co.jp/alloy/english/products/happou/index.htmn. The metal foam may comprise alloys, such as nickel, chrome, tungsten, molybdenum, ferric, or other metal(s). Examples of metal foam alloys that may be employed are MA23 nickel-chrome-tungsten-molybdenum alloy and MA600 nickel-chrome-ferric alloy from MITSUBISHI MATERIALS CORPORATION™. Another filter that may be employed is a stainless steel 40 BL3 metal felt available from BEKAERT CORPORATION™ of Marietta, Ga. available at http://www.bekaert.com/. Non-metallic solid foam, such as carbon nanofoam or organic polymers (e.g., areogels—silica, carbon, alumina, zirconia), may also be employed. The selected material is preferably chosen for operability in the integrated systems and/or for its capability of capturing effective samples of material, preferably both particle and vapor.

The metal foam 522 and/or filter 122 may be selected to achieve a desired performance. Tables 1 and 2 show examples of filtering properties, such as the relative vapor collection efficiency in the detection of an explosive (TNT) passed through a metal foam and a reference material. In the examples provided, Table 1 shows a comparison of a first metal foam (MA23 nickel-chrome-tungsten-molybdenum alloy commercially available from MITSUBISHI MATERIALS CORPORATION™) with a metal filter (stainless steel 40 BL3 metal felt commercially available from BEKAERT CORPORATION™). Table 2 shows a comparison of a second metal foam (MA600 nickel-chrome-ferric alloy commercially available from MITSUBISHI MATERIALS CORPORATION™) with the same metal filter (stainless steel 40 BL3 metal). Each of the metal foams has about a 300 micron nominal pore size and a nominal thickness of about 1 mm. Each table quantifies the recovery of the target material (TNT) collected by the filter from air passing through the filter at a given flow rate.

TABLE 1

| MA600 1.0 mm 300 um | | | |
|---|---|---|---|
| Position | TNTConc (pg/uL) | TNT recovered (ng) | Flow (L/min) |
| 1 | 3.64748 | 1.82 | 1.6 |
| 2 | 7.54742 | 3.77 | 1.538 |
| 3 | 4.86253 | 2.43 | 1.592 |
| 4 | 12.257 | 6.13 | 1.533 |
| 5 | 3.15874 | 1.58 | 1.648 |
| 6 | 4.89007 | 2.45 | 1.518 |
| A | 4.48142 | 2.24 | 1.863 |

TABLE 1-continued

MA600 1.0 mm 300 urn

| Position | TNTConc (pg/uL) | TNT recovered (ng) | Flow (L/min) |
|---|---|---|---|
| B | 3.0013 | 1.50 | 1.622 |
| C | 3.07613 | 1.54 | 1.962 |
| Average (1-6) | 3.03 | 1.65 | |
| Std. Dev. | 1.70 | 0.16 | |
| Average (A-C) | 1.76 | 1.82 | |
| Std. Dev. | 0.42 | 0.17 | |

TABLE 2

MA23 1.0 mm 300 um

| Position | TNTConc (pg/uU) | TNT recovered (ng) | Flow (L/min) |
|---|---|---|---|
| 1 | 3.42468 | 1.71 | 1.57 |
| 2 | 3.82487 | 1.91 | 1.543 |
| 3 | 4.33462 | 2.17 | 1.575 |
| 4 | 7.16527 | 3.58 | 1.494 |
| 5 | 2.62518 | 1.31 | 1.669 |
| 6 | 3.60361 | 1.80 | 1.612 |
| A | 2.51926 | 1.26 | 1.725 |
| B | 3.41094 | 1.71 | 1.87 |
| C | 2.3814 | 1.19 | 1.724 |
| Average (1-6) | 2.08 | 1.64 | |
| Std. Dev. | 0.79 | 0.12 | |
| Average (A-C) | 1.39 | 1.77 | |
| Std. Dev. | 0.28 | 0.08 | |

As shown in the tables above, the MA600 metal foam collected 72% more TNT than the 40BL3 metal felt, and the MA23 metal foam collected 50% more TNT than the 40BL3 metal felt The selected filter employed may be selected based on the ability of the fiber to recover a greater amount of the target material (TNT) that is passed therethrough. In this case, MA600 may be selected as a desired foam for use in the screeners 112a,g in order to detect trace amounts of particles on objects (e.g., 102a,b of FIGS. 1A and 1B). Other performance factors, such as cost, size, ease of use, durability, etc., may also be considered.

While specific configurations of the systems 100a,b, screening portal 101a, screening wand 101b and integrated screeners 112a,b are provided, it will be appreciated that various combinations of these devices as shown may be used. For example, the integrated screener 112a may be incorporated into screening wand 101b, and the integrated screener 112b may be used with screening portal 101a. Also, these devices may be used in combination with each other and/or other screening devices.

Figure 6:
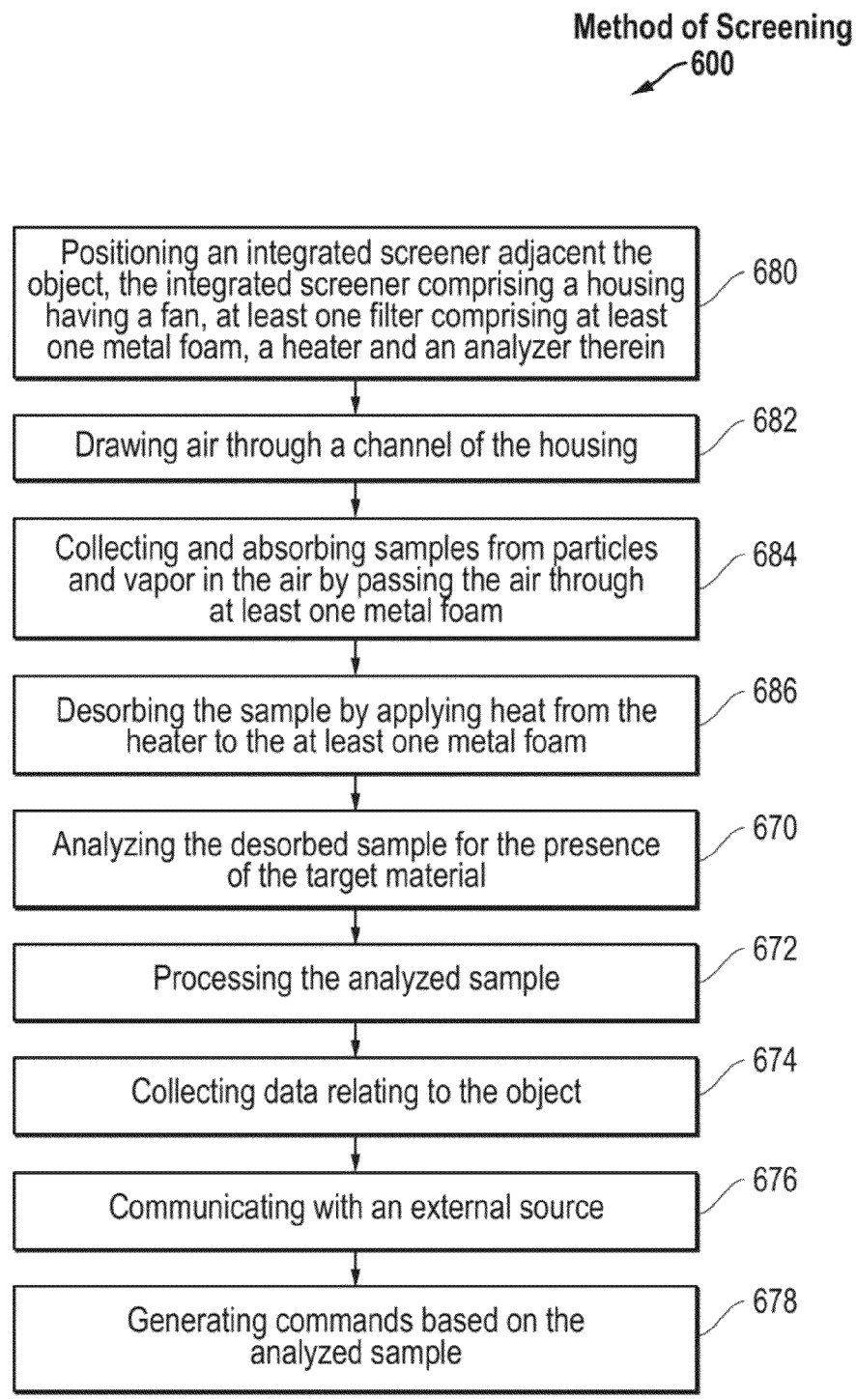
FIG. 6 is a flow chart depicting a method of screening.

FIG. 6 depicts a method 600 of screening an object, such as the objects 102a,b of FIGS. 1A, 1B. The method involves positioning 680 an integrated screener adjacent the object. Preferably, the integrated screener comprises a housing with a metal foam, a heater and an analyzer therein. The method further involves drawing 682 air into the channel using, for example, fan 120 of FIG. 2. Samples may be collected 684 from the air by passing the air through at least one filter in the channel (see, for example, air flowing through filter 122 in FIG. 2). The sample may be desorbed 686 by applying heat from the heater to the at least one metal foam. The desorbed sample may be analyzed 670 for the presence of the target material.

Additional steps may optionally be performed. For example, the analyzed sample may be processed 672 by computationally processing information obtained by the step of analyzing, data collected 674, communication with an external source performed 676, and commands generated 678 based on information related to the analyzed sample. The process may be repeated as desired. Preferably, the collection, desorption and analysis of the samples from the object are performed in a single, integrated operation. An integrated device, such as screener 112a,b may be provided for performing multiple integrated functions in a single operation and/or with a single device.

It will be understood from the foregoing description that various modifications and changes may be made in the preferred and alternative embodiments of the present invention without departing from its true spirit. For example, the apparatus may be of other shapes to facilitate flow of air about the object, or alarms or other devices may be provided.

This description is intended for purposes of illustration only and should not be construed in a limiting sense. The scope of this invention should be determined only by the language of the claims that follow. The term "comprising" within the claims is intended to mean "including at least" such that the recited listing of elements in a claim are an open group. "A," "an" and other singular terms are intended to include the plural forms thereof unless specifically excluded.

What is claimed is:

1. An integrated apparatus for screening an object for a target material, the integrated apparatus comprising:
   an integrated screener positionable in a housing positionable adjacent the object, the integrated screener comprising:
   a fan for drawing air through a channel through the housing, the air carrying particles and vapor therewith;
   at least one filter positionable in the channel of the housing for passage of the air therethrough, the at least one filter comprising at least one metal foam having:
      a plurality of pores therein for collecting and adsorbing a sample from the particles and vapor of the air passing therethrough; and
      a plurality of cut edges, each of the plurality of cut edges formed by EDM;
   a heater for applying heat to the at least one metal foam whereby the sample is desorbed from the metal foam; and
   an analyzer for detecting the target material from the sample after desorption.

2. The integrated apparatus of claim 1, wherein the at least one metal foam comprises at least one heat resistant alloy.

3. The integrated apparatus of claim 2, wherein the at least one heat resistant alloy comprises a nickel-chrome-tungsten-molybdenum alloy.

4. The integrated apparatus of claim 2, wherein the at least one heat resistant alloy comprises a nickel-chrome-ferric alloy.

5. The integrated apparatus of claim 1, wherein the at least one metal foam has a pore size of about 300 microns.

6. The integrated apparatus of claim 1, wherein the metal foam is about 1 mm thick.

7. The integrated apparatus of claim 1, wherein the housing comprises a non-conductive material.

8. The integrated apparatus of claim 7, wherein the non-conductive material comprises a ceramic.

9. The integrated apparatus of claim 7, wherein the heater comprises a pair of electrodes operatively connected to the non-conductive housing.

10. The integrated apparatus of claim 9, wherein the electrodes comprise copper.

11. The integrated apparatus of claim 1, wherein the heater comprises an electrical resistance heater.

12. The integrated apparatus of claim 1, wherein the housing comprises a handle for handheld operation.

13. An integrated apparatus for screening an object for a target material, the integrated apparatus comprising:
- an integrated screener positionable in a housing positionable adjacent the object, the integrated screener comprising:
- a fan for drawing air through a channel through the housing, the air carrying particles and vapor therewith;
- at least one filter positionable in the channel of the housing for passage of the air therethrough, the at least one filter including:
  - a first metal foam having:
    - a plurality of pores therein for collecting and adsorbing a sample from the particles and vapor of the air passing therethrough; and
    - a first pore size; and
  - a second metal foam having;
    - a plurality of pores therein for collecting and adsorbing a sample from the particles and vapor of the air passing therethrough; and
    - a second larger pore size;
- a heater for applying heat to the at least one metal foam whereby the sample is desorbed from the metal foam; and
- an analyzer for detecting the target material from the sample after desorption.

14. The integrated apparatus of claim 13, wherein the at least one metal foam comprises at least one heat resistant alloy.

15. The integrated apparatus of claim 13, wherein the at least one metal foam has a pore size of about 300 microns.

16. The integrated apparatus of claim 13, wherein the housing comprises a non-conductive material.

17. The integrated apparatus of claim 13, wherein the heater comprises an electrical resistance heater.

18. The integrated apparatus of claim 13, wherein the housing comprises a handle for handheld operation.

* * * * *